(12) United States Patent
Bartelme et al.

(10) Patent No.: US 10,786,313 B2
(45) Date of Patent: Sep. 29, 2020

(54) DEVICES AND METHODS FOR TEMPORARY MOUNTING OF PARTS TO BONE

(71) Applicant: GLOBUS MEDICAL, INC., Audubon, PA (US)

(72) Inventors: Michael Bartelme, Fort Collins, CO (US); Neil R. Crawford, Chandler, AZ (US); Mitchell A. Foster, Scottsdale, AZ (US); Chris Major, Philadelphia, PA (US); Nicholas Theodore, Ruxton, MD (US)

(73) Assignee: Globus Medical, Inc., Audubon, PA (US)

( * ) Notice: Subject to any disclaimer, the term of this patent is extended or adjusted under 35 U.S.C. 154(b) by 232 days.

(21) Appl. No.: 16/056,744

(22) Filed: Aug. 7, 2018

(65) Prior Publication Data

US 2018/0338800 A1    Nov. 29, 2018

Related U.S. Application Data

(63) Continuation of application No. 14/824,586, filed on Aug. 12, 2015, now Pat. No. 10,080,615.

(51) Int. Cl.
*A61B 34/20* (2016.01)
*A61B 90/50* (2016.01)
(Continued)

(52) U.S. Cl.
CPC .............. *A61B 34/20* (2016.02); *A61B 17/56* (2013.01); *A61B 90/10* (2016.02); *A61B 90/39* (2016.02); *A61B 90/50* (2016.02); *A61B 2034/2068* (2016.02); *A61B 2090/3916* (2016.02); *A61B 2090/3983* (2016.02); *A61B 2090/3991* (2016.02)

(58) Field of Classification Search
CPC ..... A61B 19/00; A61B 19/201; A61B 19/203; A61B 19/20; A61B 19/22; A61B 19/5244; A61B 17/56; A61B 17/3403
See application file for complete search history.

(56) References Cited

U.S. PATENT DOCUMENTS 4,150,293 A    4/1979   Franke
5,236,432 A *  8/1993   Matsen, III ............ A61B 17/15
                                                    606/88
(Continued)

FOREIGN PATENT DOCUMENTS

EP    1129668 A1    9/2001
FR    2725126 A1    4/1996
(Continued)

OTHER PUBLICATIONS

US 8,231,638 B2, 07/2012, Swarup et al. (withdrawn)

*Primary Examiner* — Vi X Nguyen

(57) ABSTRACT

Devices and methods for temporarily affixing a surgical apparatus to a bony structure. The temporary mount includes a base member having a top face configured to be impacted by an insertion device and a plurality of elongated prongs extending downwardly from the base member and configured to engage a bony structure. The prongs are separated a distance from one another, and the prongs are configured to move inwardly toward one another when driven downward into the bony structure.

16 Claims, 7 Drawing Sheets

(51) Int. Cl.
*A61B 90/10* (2016.01)
*A61B 17/56* (2006.01)
*A61B 90/00* (2016.01)

(56) References Cited

U.S. PATENT DOCUMENTS

| | | | |
|---|---|---|---|
| 5,246,010 A | 9/1993 | Gazzara et al. |
| 5,354,314 A | 10/1994 | Hardy et al. |
| 5,397,323 A | 3/1995 | Taylor et al. |
| 5,487,739 A * | 1/1996 | Aebischer | C12N 11/04 604/890.1 |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,042,582 A | 3/2000 | Ray |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,296,643 B1 | 10/2001 | Hopf et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,336,928 B1 | 1/2002 | Guerin et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,558,617 B2 | 7/2009 | Vilsmeier |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |

(56) References Cited

U.S. PATENT DOCUMENTS

| | | |
|---|---|---|
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |

(56) References Cited

U.S. PATENT DOCUMENTS

| | | |
|---|---|---|
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |

(56) References Cited

U.S. PATENT DOCUMENTS

| | | |
|---|---|---|
| 2005/0096502 A1 | 5/2005 | Khalili |
| 2005/0119639 A1 | 6/2005 | McCombs et al. |
| 2005/0143651 A1 | 6/2005 | Verard et al. |
| 2005/0171558 A1 | 8/2005 | Abovitz et al. |
| 2005/0267480 A1 | 12/2005 | Suddaby |
| 2006/0015018 A1 | 1/2006 | Jutras et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2007/0276370 A1 | 11/2007 | Altarac et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |

(56) References Cited

U.S. PATENT DOCUMENTS

| | | |
|---|---|---|
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0142628 A1 | 5/2014 | Traynely et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0277516 A1 | 9/2014 | Miller et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucker et al. |

FOREIGN PATENT DOCUMENTS

| | | |
|---|---|---|
| FR | 2754702 | 4/1998 |
| FR | 2941364 A1 | 7/2010 |
| JP | 2001502572 A | 2/2001 |
| JP | 2002541966 A | 12/2002 |
| JP | 2008507361 A | 3/2008 |
| WO | 2004069073 A2 | 8/2004 |
| WO | 2006012491 A1 | 2/2006 |

* cited by examiner

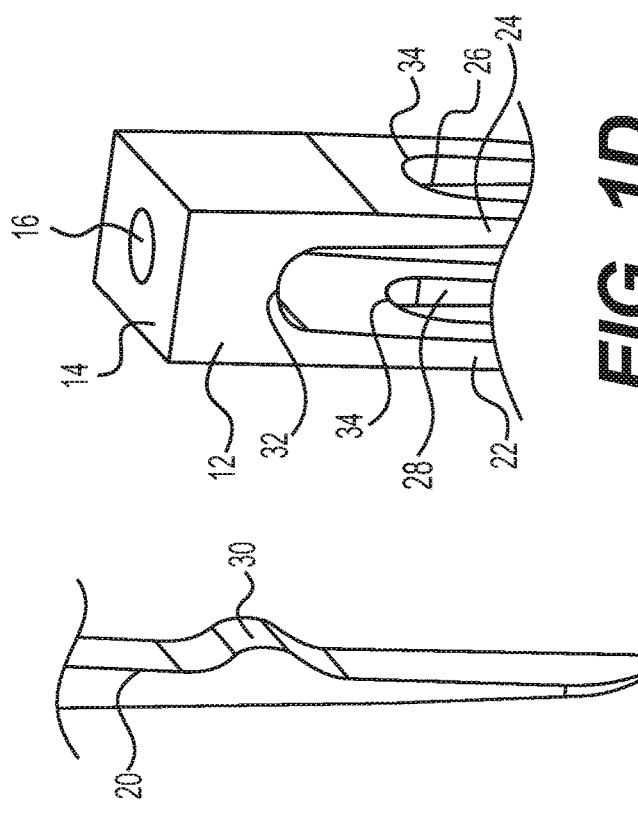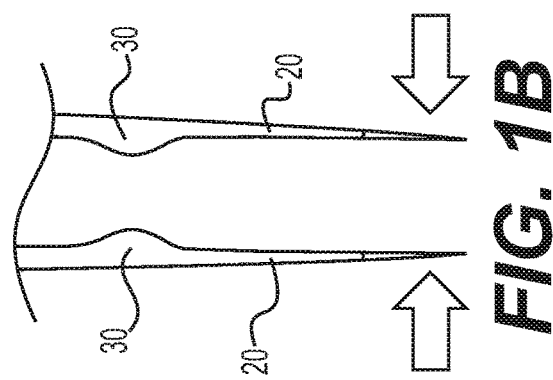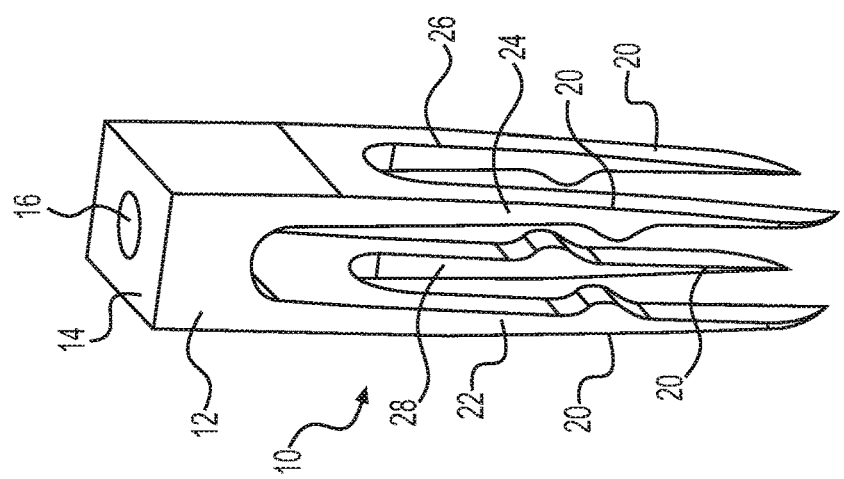

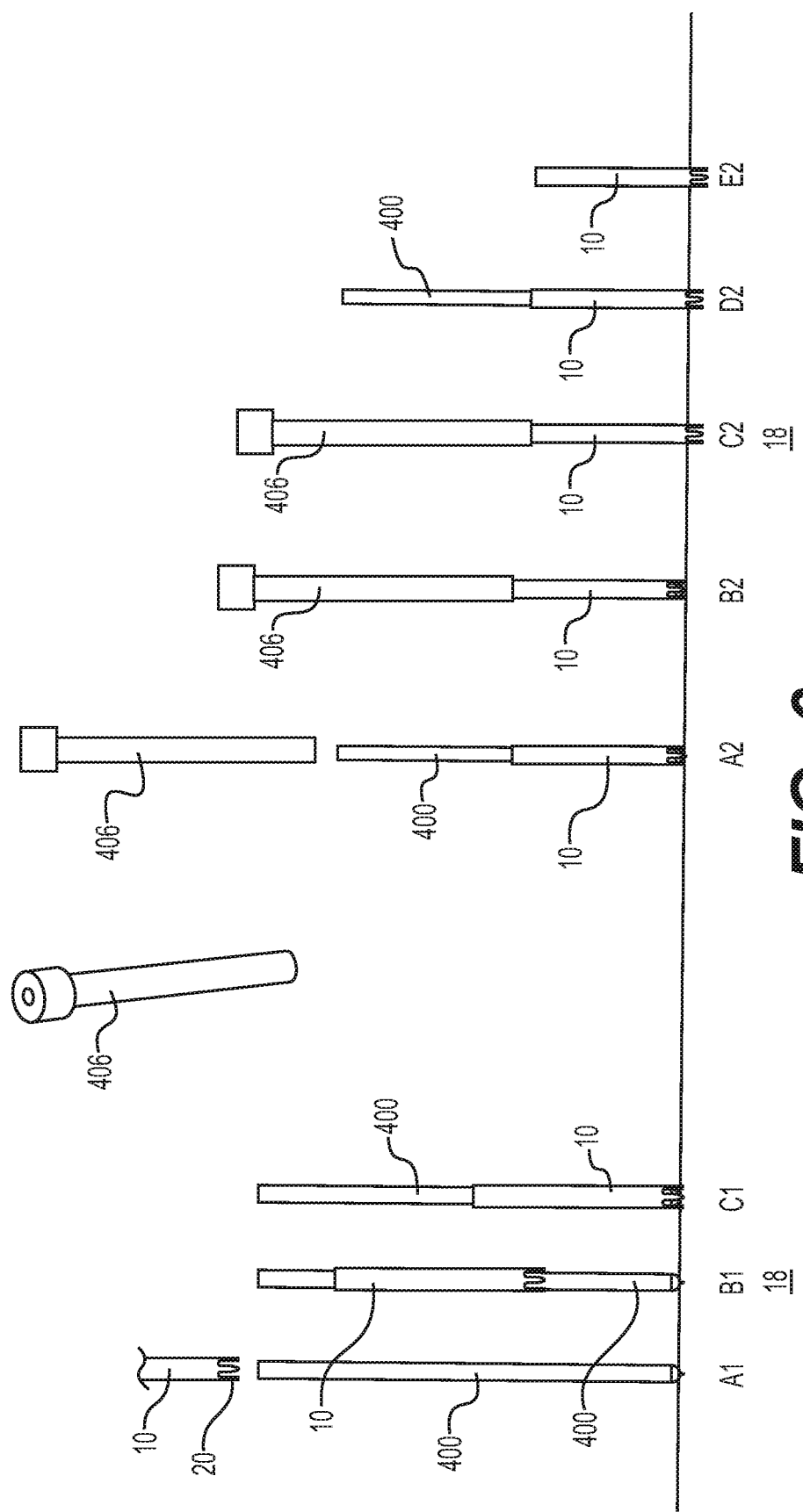

DEVICES AND METHODS FOR TEMPORARY MOUNTING OF PARTS TO BONE

CROSS-REFERENCE TO RELATED APPLICATION

The present application is a Continuation of U.S. patent application Ser. No. 14/824,586, filed on Aug. 12, 2015, the contents of which are incorporated herein in their entirety by reference for all purposes.

FIELD OF THE INVENTION

The present disclosure generally relates to devices and methods to temporarily mount an apparatus to bone. For example, these temporary mounts may be suitable for attaching an apparatus, such as a trackable reference array, to a bony structure in a patient's body to provide a reference point during surgical navigation.

BACKGROUND OF THE INVENTION

During surgery, it may be necessary to temporarily mount an apparatus to exposed bone. For example, when using surgical navigation, it may be necessary to attach a tracker, such as a trackable reference array of optical markers, to the patient for accurately tracking the position of tools relative to the surgical site. If bone is the surgical target, such as when inserting a bone screw or the like, then attaching the reference array to bone provides better accuracy than attaching the reference array to surrounding soft tissues and more accurately tracks the position of the surgical tools relative to the bone. After the surgical procedure is completed (e.g., installing bone screws, rods, implants, and the like), the mounted tracker is typically removed.

Current methods for temporarily attaching trackers, reference arrays, or other devices to bone may include one or more of the following: screw-based mounting devices, in which one or more screws are inserted to hold the device to bone; clamp-based mounting devices, in which teeth and jaws of a clamp or clamps are tightened around bony prominences; or spike-based devices, in which one or more spikes are driven into bone with a mallet. These devices, however, may only provide for a single point of fixation to the bone, thereby providing a weak attachment to the bone and potentially compromising the accuracy of the tracker. In addition, traditional devices may be accidentally advanced too far into the bony structure, which can damage the bone or surrounding areas or make it difficult to remove the temporary mounting device, which is embedded too deeply into the bone, after the procedure is completed.

SUMMARY OF THE INVENTION

To meet this and other needs, devices, systems, kits, and methods for temporarily mounting an apparatus, such as a tracker, to bony structures are provided. In particular, the temporary devices may provide for multiple points of fixation to the bone, thereby providing a strong attachment to the bone and improving the accuracy of an attached apparatus, such as a tracker for surgical navigation. The temporary mounting devices may also include features, such as stops including protrusions and arched regions, for example, which prevent the temporary mounting device from accidentally being advanced too far into the bony structure. The design of the temporary mounts can help to protect the bone and surrounding areas and can be easier to remove from the bone when the surgical navigation and/or surgical procedure are completed.

According to one embodiment, a mount for temporarily affixing a surgical apparatus to a bony structure (e.g., one or more vertebrae of a spine) includes a base member having a top face configured to be impacted by an insertion device, and a plurality of elongated prongs extending downwardly from the base member and configured to engage a bony structure. Each of the plurality of prongs are separated a distance from one another. The prongs may be configured to move inwardly toward one another when driven downward into the bony structure by the insertion device. The mount has multiple points of fixation with the bony structure to provide a strong and reliable attachment to the bone. For example, the plurality of prongs may include two or more, three or more, or four or more prongs extending from the base member. The prongs may be elongated in the form of legs, tines, spikes, pins, or the like.

The temporary mount may include one or more of the following features, for example. Each of the plurality of prongs may include a protrusion extending therefrom configured to act as a stop to prevent over-insertion of the mount in the bony structure. The protrusions may be in the form of hill-shaped prominences positioned along the length of the prong (e.g., spaced apart from a distal most end). The plurality of elongated prongs may extend a length greater than a length of the base member (e.g., the prongs are longer than the base member portion of the mount such that the height of the device is primarily due to the height of the prongs). The plurality of elongated prongs may be in the form of a first prong and a second prong, and a transition from the first prong to the second prong may be arched or curved to act as an ultimate stop to prevent over-insertion of the mount in the bony structure. An arched stop may be provided between each prong. The plurality of elongated prongs may include a first prong, a second prong, a third prong, and a fourth prong, where a first arched portion between the first prong and the second prong has a first distance from the top face, and a second arched portion from the second prong to the third prong has a second distance from the top face, the second distance being different from than the first distance. In particular, the second distance may be greater than the first distance or vice versa. The arched portions on opposite sides of the device may be the same or substantially equivalent. In some embodiments, the mount may also include an outer sleeve having a hollow interior configured to engage an outer surface of the base member and/or a portion of one or more outer surfaces of the prongs. The outer sleeve may be configured to slide or rotate, for example, in order to compress the prongs inwardly toward one another. Each of the plurality of prongs may have a textured inner surface configured to resist extraction from the bone. Each of the plurality of prongs may have a sharpened distal-most tip configured to penetrate the bony structure. When the base member is impacted by the insertion device, the temporary mount may provide an audible sound, as each of the prongs is driven downward, and the frequency of the audible sound may change indicating the relative position of the mount in the bone (e.g., when the mount is fully seated in the bone structure). The mount is configured to hold and engage a portion of a trackable reference array, which may assist in surgical navigation, for example, with a surgical robot.

According to another embodiment, a kit may include a plurality of temporary mounts of different sizes and different configurations. In addition, the kit may include one or more devices suitable for surgical navigation, for example, including a trackable array, and configured to be attachable to the temporary mounts; one or more central shafts configured to guide the mount through soft tissue and into contact with bone; one or more driving sleeves configured to apply a force to the driving sleeve to cause the temporary mount to advance into the bone; one or more insertion devices, such as impact drivers, mallets, or the like, configured to engage the mounts, the central shafts, and/or the driving sleeves; one or more removal devices, such as slap hammers, slide hammers, or the like, configured to retrieve and extract the temporary mounts from the bone; and other tools and devices, which may be suitable for surgery.

According to another embodiment, a system for temporarily affixing a surgical apparatus to a bony structure includes at least one temporary mount and a least one tracking device, such as a trackable reference array for surgical navigation. The temporary mount includes a base member having a top face configured to be impacted by an insertion device, and a plurality of elongated prongs extending downwardly from the base member and configured to engage a bony structure, wherein each of the plurality of prongs are separated a distance from one another, and wherein the prongs are configured to move inwardly toward one another, for example, when driven downward into the bony structure. The trackable reference array is connected to the base member of the temporary mount, for example, at an opening in the top face of the base member.

According to yet another embodiment, a method of temporarily affixing a surgical apparatus to a bony structure includes (a) inserting a central shaft through soft tissue and into contact with bone; (b) inserting a cannulated temporary mount over the central shaft and moving the temporary mount downwardly and into contact with the bone, the cannulated temporary mount having a first end configured to be engaged by an insertion tool and a second end terminating as a plurality of elongated prongs configured to engage bone, wherein each of the plurality of prongs are separated a distance from one another, and wherein the prongs are configured to move inwardly toward one another when driven downward into the bony structure; (c) optionally, positioning a driving sleeve over the central shaft and into contact with the first end of the temporary mount; (d) applying a force to the temporary mount to advance at least a portion of the prongs into the bone, optionally, by applying a force to the driving sleeve; and (e) optionally, removing the driving sleeve and the central shaft to leave the temporary mount embedded in the bone. In one embodiment, the temporary mount further includes an outer sleeve, and the method additionally comprises (f) optionally, rotating the outer sleeve in order to compress the prongs inwardly toward one another to further secure the mount to the bone. The method may also include (g) attaching a portion of a trackable reference array for surgical navigation to the temporary mount and/or (h) removing the temporary mount from the bone after the surgical navigation is complete.

BRIEF DESCRIPTION OF THE DRAWING

A more complete understanding of the present invention, and the attendant advantages and features thereof, will be more readily understood by reference to the following detailed description when considered in conjunction with the accompanying drawings wherein:

FIGS. 1A-1E depict a temporary mounting apparatus including multiple prongs or tines configured to engage a bony structure according to one embodiment;

FIG. 6 illustrates the components and a series of steps, which may be used to install a temporary mounting apparatus in the bone.

DETAILED DESCRIPTION

Figure 1E:
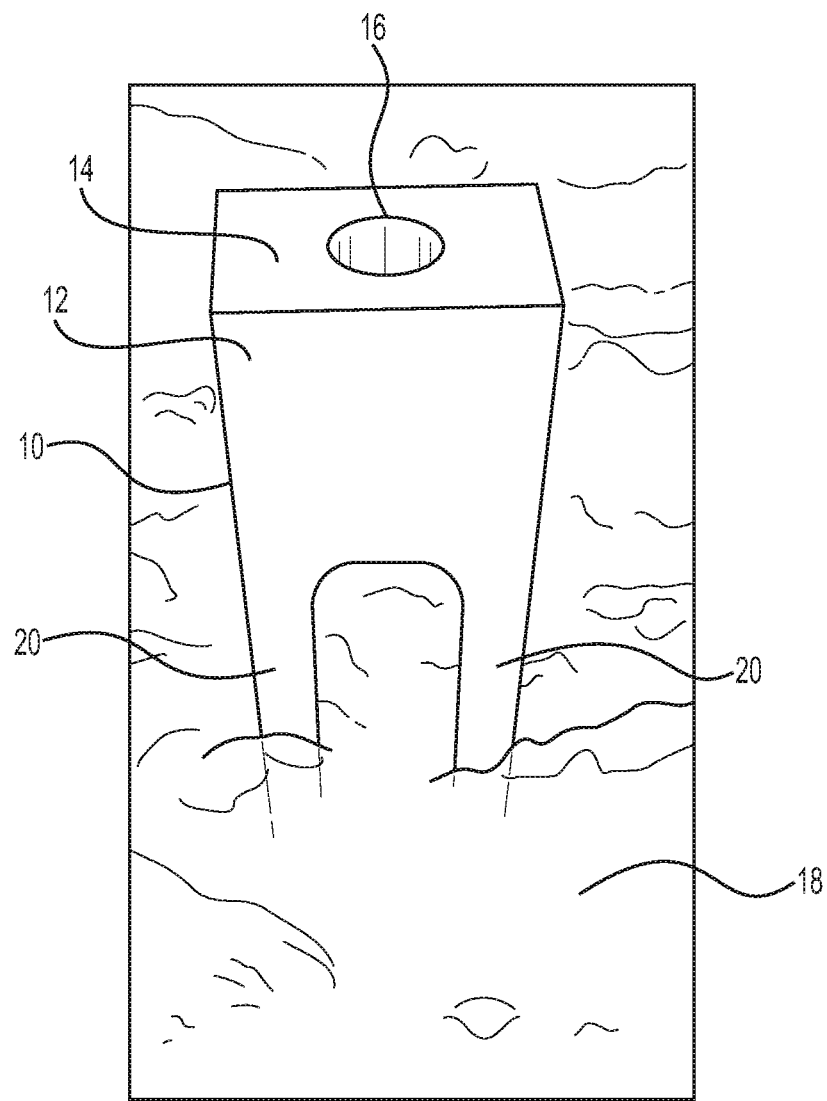

Embodiments of the disclosure are generally directed to devices, systems, kits, and methods for temporarily mounting an apparatus, such as a tracker for surgical navigation, to bony structures. Specifically, the temporary mounts may include a plurality of prongs, legs, spikes, tines, or the like, extending from a base member, which provide for multiple points of fixation to the bony structure. The bony structure may include any bones, bony segments, bony portions, bone joints, or the like of a patient. For example, the bony structure may include areas from a bone from the spine, such as a vertebra, a hip bone, such as an ilium, a leg bone, such as a femur, or a bone from an arm, such as a distal forearm bone or a proximal humerus, or any other bone in a mammal. In an exemplary embodiment, the bony structure or bone includes one or more vertebrae in the spinal column of a human patient. Providing for multiple points of fixation allows for a stronger attachment to the bone and may maintain or improve the positional accuracy of an attached apparatus, such as a tracker for surgical navigation.

The temporary mounting devices may also include features, such as stops, for example, to prevent or minimize the occurrence of the temporary mounting device from being advanced too far into the bony structure. One or more features on the temporary mounting devices can also help to protect the bone and surrounding areas and may make it easier for the surgeon to remove the temporary mounting device from the bone when the surgical navigation has been completed.

The embodiments of the disclosure and the various features and advantageous details thereof are explained more fully with reference to the non-limiting embodiments and examples that are described and/or illustrated in the accompanying drawings and detailed in the following description. The features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar features and structures throughout the several views of the drawings.

According to a first embodiment, a spike-based device may include multiple prongs or tines extending from a rigid base. For example, a mount for temporarily affixing a surgical apparatus to a bony structure (e.g., vertebrae of a spine) includes a base member having a top face configured to be impacted by an insertion device, and a plurality of elongated prongs extending downwardly from the base member and configured to engage a bony structure. Each of the plurality of prongs are separated a distance from one another. The prongs may be configured to move inwardly toward one another, for example, when driven downward into the bony structure or thereafter. The mount has multiple points of fixation with the bony structure to provide a strong and reliable attachment to the bone. This device has several unique features that give it advantages when used to temporarily attach a reference array or other device to bone.

Referring now to the drawing, FIGS. 1A-1E depict a temporary mounting apparatus 10 including multiple prongs 20 configured to engage a bony structure 18. Turning to FIG. 1A, a perspective view of the temporary mounting apparatus 10 is shown, which includes a base member 12 with a plurality of prongs 20 extending downwardly therefrom. The base member 12 preferably forms a rigid base or frame for the mounting apparatus 10. The top face 14 of the base member 12 may connect with one or more adjoining side faces (e.g., in this case, four adjoining side faces). For example, the base member 12 may form a partially cube-shaped or rectangular-shaped block. Although four sides are depicted, the base member 12 may include more or less sides. Thus, the top face 14, when viewed from above, may be substantially square shaped (e.g., all of the sides are of equal size), rectangular-shaped (e.g., two of the sides are of equal size), or of any other suitable shape. Each of the adjoining side faces may form a corner edge therebetween. Each of the corner edges may be sharp, beveled, rounded, or the like.

The base member 12 may have a top face 14 configured to receive impaction forces from an insertion tool, such as an impact driver, mallet, or the like. The top face 14 may be substantially flat, curved, angled, for example, or of other suitable shape or contour. In an exemplary embodiment, the top face 14 of the device 10 is flat and can be a suitable surface to strike the device 10 with an impact driver or mallet, for example. The top face 14 of the base member 12 may include an opening or aperture 16. The aperture 16 extends partially or completely through the base member 12. When extending completely therethrough, the aperture 16 may provide for a cannulated device 10. The aperture 16 may be sized and dimensioned to receive, for example, a guide wire, post, or central shaft, discussed in more detail herein, to insert the device 10 in a minimally invasive surgical procedure. For example, a post can be previously mounted to the spike 10, extending upward therefrom, before the device 10 is driven into bone 18. The device 10 can be driven by striking this post, which may be easier than striking the flat part shown, especially when driving the spike 10 down through regions surrounded by thick tissues.

After the mount 10 is in place seated in bone 18, attachments can be mounted to a portion of the device 10 in various ways. In particular, the hole or aperture 16 may also be sized and dimensioned to removably connect a portion of a tracker (not shown), such as a trackable reference array of optical markers, for surgical navigation and/or robotic systems. Surgical navigation systems and trackable markers are described in more detail in U.S. Pat. Nos. 8,010,181, 8,219, 177, 8,219,178, 9,078,685, and U.S. Publication Nos. 2013/ 0345718, 2014/0275955, 2014/0378999, 2015/0032164, which are incorporated by reference herein in their entireties for all purposes. The aperture 16 may be non-threaded, partially threaded, or fully threaded along its length, for example. If the aperture 16 is threaded, a separate device mounted to or having a bolt or shaft can be attached. Alternately, a keyed slot, snap-on attachment, clamp, or other means can be used to attach other devices, such as the reference array, to the device 10.

As shown in FIG. 1A, a plurality of prongs 20 extend from the base member 12. The prongs 20 may be configured to penetrate and temporarily engage bone 18, for example, as shown in FIG. 1E. In particular, the prongs 20 may be configured to secure the mount 10 to the bone 18 for the duration of the surgical procedure and may be configured to be removed from the bone 18 once the surgical operation is complete. Thus, the mounts 10 are not intended to be permanently affixed to the bone 18. The plurality of prongs 20 may include two or more, three or more, four or more prongs, five or more prongs, or six or more prongs, for example. The prongs 20 may be in the form of tines, legs, spikes, pins, or the like. The plurality of prongs 20 are preferably elongated such that they have a length substantially greater than their width. The prongs 20 may have a length or height greater than the length or height of the base member 12 (e.g., about twice the height of the height of the base member 12). Thus, the prongs 20 may make up a substantial portion of the height of the device 10. Each of the prongs 20 may terminate at a distal end configured to penetrate the bony structure 18. In one embodiment, the prongs 20 are in the form of tines having sharp distal ends. It is also envisioned, however, that the prongs 20 may have blunt, chamfered, or beveled distal ends depending on the design of the prongs 20.

In one embodiment, four separate prongs 20 may be projecting from each corner of a cubic base member 12 and extending generally away from the top face 14. With continued reference to FIG. 1A, the four prongs 20 may include a first tine 22 extending downwardly from a first corner of the base member 12, a second tine 24 extending downwardly from a second corner of the base member 12, a third tine 26 extending downwardly from a third corner of the base member 12, and a fourth tine 28 extending downwardly from a fourth corner of the base member 12. Thus, the temporary mounting apparatus 10 may be in the form of a 4-pronged spike. Although four tines 22, 24, 26, 28 will be described in more detail herein with reference to the temporary mounting apparatus 10, it is envisioned that the position and configuration of the tines may be varied or changed as would be appreciated by one of ordinary skill in the art.

With further reference to FIG. 1A, the tines 22, 24, 26, 28 extend downwardly from the base member 12 at each respective corner. Each corner edge from the base member 12 extends continuously along each respective tine 22, 24, 26, 28. Thus, a plurality of sharp edges extend from a first end (e.g., the top face 14 configured to receive impaction from an insertion tool) of the device 10 to a second end (e.g., the distal ends of the tines 22, 24, 26, 28 configured to penetrate and engage the bone 18). Each of tines 22, 24, 26, 28, when viewed from one of the sides, may be tapered such that it has a wider section proximate to the base member 12 and progressive narrows toward its distal end. The prongs 20 of the spike 10 may be intentionally designed thin enough that they plastically deform or curl while the device 10 is driven into bone 18. This curling can lead to improved strength and rigidity of fixation because the prongs 20 become intertwined with the bone 18.

The device 10 may be constructed from a single piece of suitably strong and rigid material. The material is preferably biocompatible. For example, the material may include metals, such as stainless steel, titanium, or titanium alloys. Dimensions of the device 10 may be about 10 mm×15 mm×60 mm but could be smaller or larger as needed depending on the bone and application.

As best seen in the side view in FIG. 1B, a pair of prongs 20 (representing each pair of tines 22, 24, 26, 28 from each respective side view) are separated a distance from one another. The prongs 20 may be slightly inwardly angled. The amount of lateral spreading or squeezing force that can be generated by the prongs 20 as the device 10 is driven downward into the bone 18 can be influenced by the design of the taper of the four prongs 20, for example. When driven vertically downward, the prongs 20 move toward each other as depicted by the arrows in FIG. 1B. Depending on the circumstance, it may be desirable to have the prongs 20 move toward each other, away from each other, or remain unchanged. In an exemplary embodiment, the prongs 20 are configured to move inwardly toward one another when driven downward into the bony structure or thereafter in order to provide a strong and reliable attachment to the bone 18.

Another feature of the 4-prong spike 10 is that the narrow and elongated prongs 20 tend to ring musically. In other words, when device 10 is struck by the impact driver or mallet, the device emits a frequency or audible sound wave. The audible sensation of a frequency is commonly referred to as the pitch of a sound. A high pitch sound corresponds to a high frequency sound wave and a low pitch sound corresponds to a low frequency sound wave. Most people are capable of detecting a difference in frequency between two separate sounds, and thus, different pitches. As each prong 20 is driven downward and becomes encased more and more in the bone 18, the frequency of the ringing noise, as the device 10 is struck with the mallet, for example, changes. For example, as the device begins to enter the bone 18, the frequency may provide a lower pitch. As the device 10 becomes more encased in the bone 18, however, the frequency changes to provide a higher pitch. This ringing quality can act as a feedback mechanism to let the surgeon know the position or depth of the device 10 in the bone 18. Moreover, a higher pitch may let the surgeon know that the device 10 is fully and rigidly seated in the bone 18.

As best seen in the close up view of the prong 20 (e.g., representing each of the tines 22, 24, 26, 28) in FIG. 1C, the prong 20 may have a protrusion 30, such as a hill-shaped protrusion or hill-shaped prominence, positioned along a length of the prong 20. For example, the protrusion 30 may be positioned about half-way between the distal end of the prong 20 and where the prong 20 extends from the base member 12. These protrusions may be positioned at the same location or different locations along each of the prongs 20. In one embodiment, the hill-shaped prominence 30 is roughly 10-20 mm from the distal tips of the prongs 20. The protrusions 30 may face substantially inwardly toward a central cavity defined by the prongs 20. For example, the protrusion 30 on the first tine 22 may face a similar protrusion 30 on the second tine 24. Similar, protrusion 30 on the fourth tine 28 may face a similar protrusion 30 on the third tine 26. Although only a single protrusion 30 is depicted on each prong 20, each prong 20 may include more or less protrusions along their lengths and at varied positions along their lengths.

These prominences or protrusions 30 are configured, at least in part, to act as a stop to prevent over-insertion of the device 10 into the bone 18. As the device 10 is driven downward and when bone 18 reaches these prominences or protrusions 30, the device 10 stops or slows. While it is still possible to drive the device 10 beyond this point, more effort is needed. Making these prominences or protrusions 30 as small hills instead of flat buttresses allows one or more of the prongs 20 to continue to be advanced if there is an irregularity of the bony surface 18. Additionally, as the device 10 is driven downward, the wedging action of these prominences 30 against bone 18 increase the rigidity and holding strength.

As shown in the close up perspective view of the base member 12 in FIG. 1D, transitions 32, 34 from one prong 20 to another act as ultimate stops. In particular, the transitions 32, 34 can be in the form of arches, curves, arcs, catenaries, or the like. The arches or curves may be normal or irregular in shape. The arched portions of the transitions 32, 34 may have an apex substantially at a central point between two adjacent prongs 20. In particular, arched transition 32 from the first tine 22 to the second tine 24 has a first distance from the top face 14. The same arched transition 32, not visible in the views, is present from the third tine 26 to the fourth tine 28. Arched transition 34 from the second tine 24 to the third tine 26 has a second distance from the top face 14. The same arched transition 34 is present from the fourth tine 28 to the first tine 22. The second distance to arched transitions 34 is greater than the first distance to arched transitions. It is also envisioned that the distances may be the same or different for each of the transitions 32, 34 between adjacent prongs 20.

When driven far enough to reach these stops or transitions 32, 34, further advancement of the device 10 is halted and device 10 cannot be driven farther without considerable effort. These stops can be designed to be positioned to act as safety stops to prevent the user from driving the device 10 into unsafe regions, such as nerves or the spinal canal. The transitional regions of the device 10 are formed as arches instead of corners because this design allows the prongs 20 to spread or squeeze horizontally (e.g., away from or toward one another) as the device 10 is driven downward. Horizontal squeezing of the prongs 20 against the elastic resistance of the bending metal creates a compressive force on the bone 18 between the prongs 20, thereby improving the rigidity of the device 10 and attachment to the bone 18. These transition portions 32, 34 of the device 10 also can act as a prying point when the surgeon is ready to remove the device 10. That is, a removal tool, such as a screwdriver or similar tool, can be forced under these arched regions 32, 34 and used to pry the device 10 upward to dislodge it from the bone 18.

As best seen in FIG. 1E, the device 10 may be driven downward by striking the top surface 14 or a post extending therefrom, for example, with a mallet (not shown). When correctly mounted, all four of the tines 22, 24, 26, 28 are secured through the cortical shell and into the cancellous bone of a vertebral body. The four tines 22, 24, 26, 28, as opposed to one spike which is traditionally used, gives the device 10 better holding strength than a single spike or nail because of the more numerous penetration points in the bone 18 and the unique features described herein.

Figure 2:
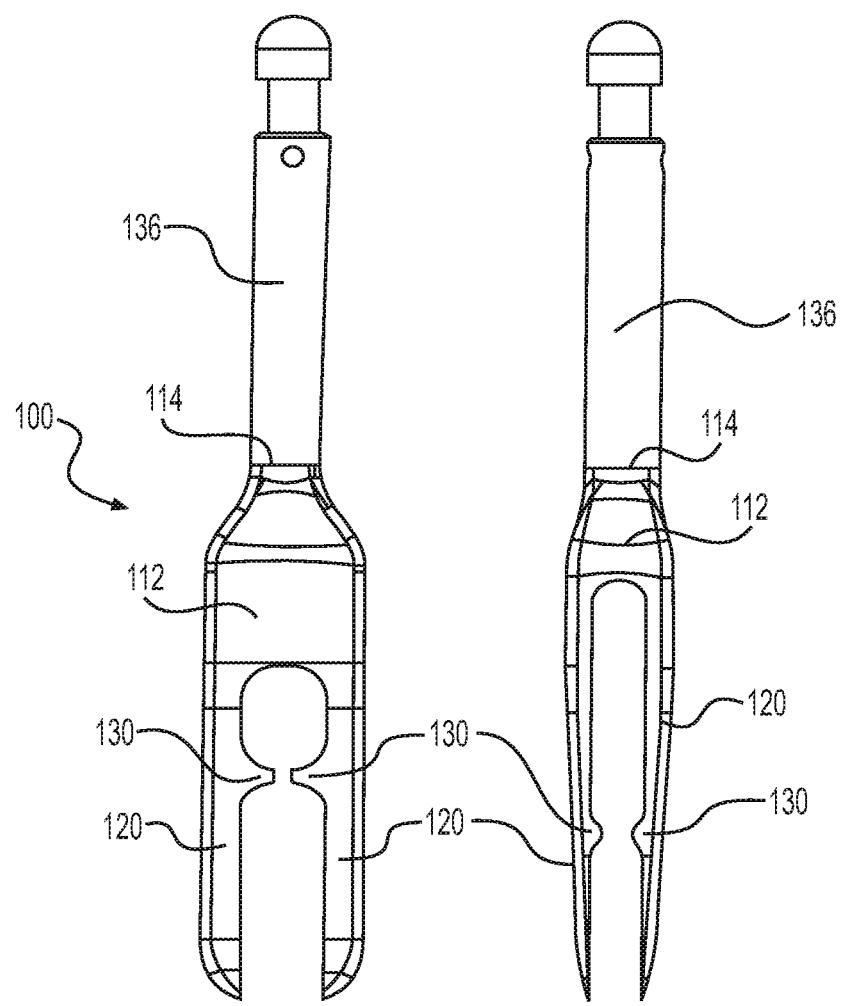
FIG. 2 depicts a temporary mounting apparatus with multiple prongs or tines according to another embodiment.

According to another embodiment, FIG. 2 depicts a front view and a side view of a temporary mounting apparatus 100 including a plurality of prongs 120 extending downwardly from a base member 112 and a post 136 extending upwardly therefrom. The top face 114 of the base member 112 connects with four adjoining side faces having beveled or rounded edges. In this embodiment, the top face 114 is smaller in width than the remainder of the base member 112. The top face 114 is configured to receive a fixed or removable post 136, for example, in an aperture (not shown) similar to aperture 16 described herein. For example, the post 136 can be removably mounted to the base member 112, extending upward therefrom, before the device 100 is driven into bone 18. The spike 100 can be driven by striking this post 136, which may be easier than striking the base member 112 directly, especially when driving the device 100 down through regions surrounded by thick tissues. In this embodiment, the prongs 120 have also been modified such that the prongs 120 have a wider cross section on one side than another. In addition, the hill-shaped prominences 130 have been elongated and positioned at different locations along the length of the prongs 20.

Figure 3A:
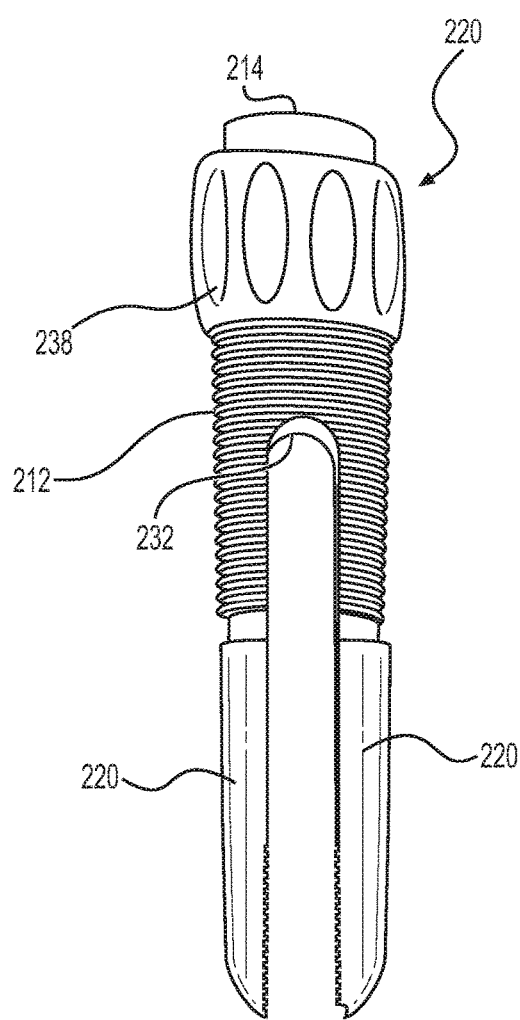
FIGS. 3A-3B show a temporary mounting apparatus with prongs that are compressible by an outer sleeve according to another embodiment.
Figure 3B:
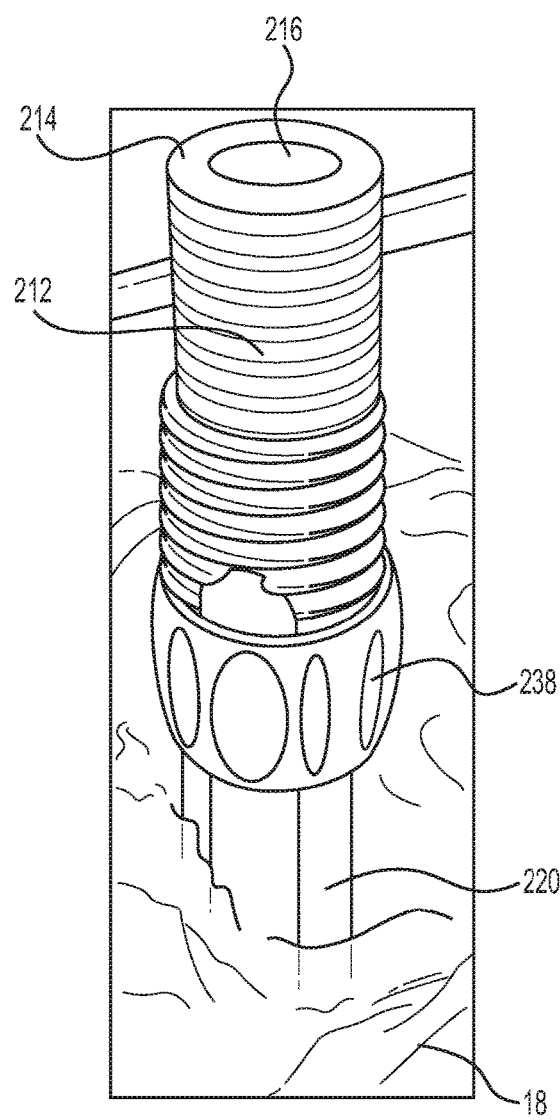

According to yet another embodiment, FIGS. 3A-3B show a temporary mounting apparatus 200 with prongs 220 that are compressible by an outer sleeve 238. In this embodiment, substantially parallel prongs 220 extend from base member 212. The base member 212 has a top face 214, when viewed from above, that may be substantially round or oval in shape. The base member 212 and prongs 220 may form a substantially cylindrically shaped device 200. The temporary mount 200 incorporates outer sleeve 238 to facilitate compressing bone 18 between the prongs 220 of the device 200. The outer sleeve 238 may be in the form of a nut, annular ring, collar, or the like having a central hollow portion extending therethrough and configured to receive a portion of the base member 212. The outer sleeve 238 may have a textured outer surface to facilitate gripping and rotating the sleeve 238 about the device 200. The base member 212 and a portion of the prongs 220 may be threaded to receive the outer sleeve 238, and the sleeve 238 may have a corresponding inner thread (not visible in the drawing). The threaded portion of the base member 212 may be of varying diameter (e.g., having a smaller diameter proximate the top face and a larger diameter proximate the prongs 220). As shown, distal portions of the outer surfaces of the prongs 220 may be substantially smooth to improve penetration into the bone 18 and to limit the amount of compression by the sleeve 238.

The top face 214 of the base member 212 may include an opening or aperture 216, which extends partially or completely through the base member 212. Thus, the device 200 may be fully cannulated. The aperture 16 may be sized and dimensioned to receive, for example, a guide wire, post, or central shaft for guiding the device 200 and/or may be sized and dimensioned to removably connect to a portion of a tracker, such as a trackable reference array, for a surgical navigation system.

Similar to devices 10 and 100, the device 200 could initially be malleted into place. Subsequently, the outer sleeve 238 would be activated, for example by sliding or rotating the outer sleeve 238, to move the outer sleeve 238 in a first direction toward the prongs 20, in order to compress the prongs 220 inwardly toward one another. When the temporary mounting apparatus 200 is to be removed, the outer sleeve 238 could be slid or rotated to move the outer sleeve 238 in a second direction, opposite the first direction and away from the prongs, in order to release the prongs 220. Such a mechanism might be especially useful if the prongs 220 are forced down over a bony prominence, such as the spinous process, and then need to be secured further by compressing and clamping the bone 18 between the prongs 220. As can be seen in FIGS. 3A and 3B, one version of this design has the inner portion of the sleeve 238 threaded so that when the outer nut or sleeve 238 is rotated and advanced downward toward the prongs 220, the prongs 220 of the device 200, if initially splayed outward, are forced inward to the diameter of the nut or sleeve 238.

Figure 4A:
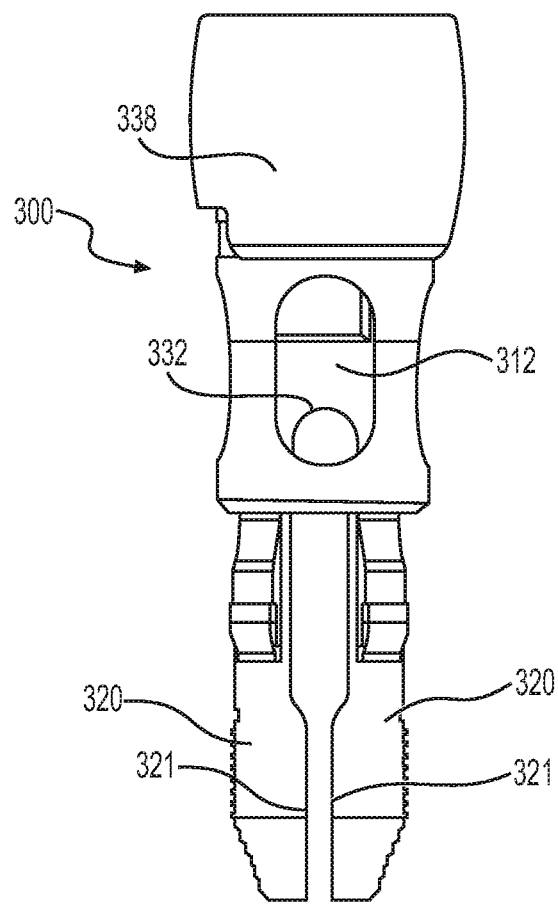
FIGS. 4A-4B show a temporary mounting apparatus with prongs that are compressible by an outer sleeve according to yet another embodiment.
Figure 4B:
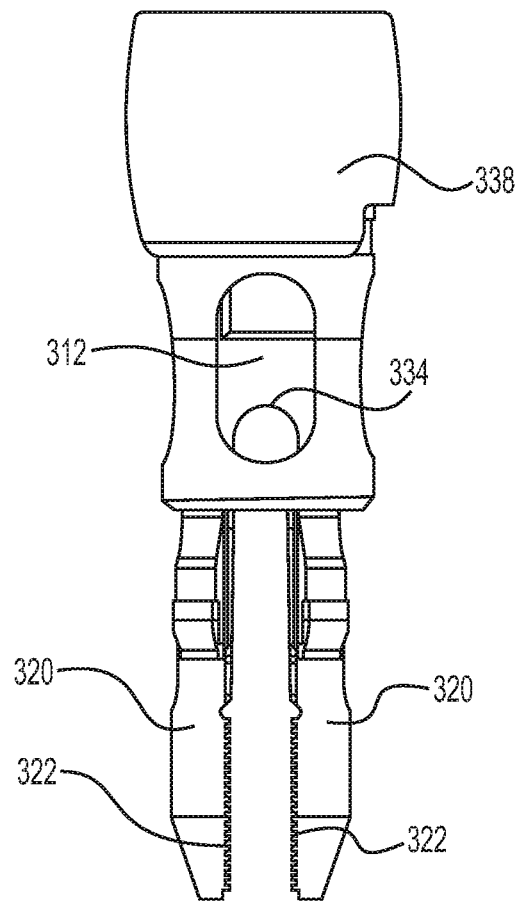

Similar to device 200, FIGS. 4A-4B depict a temporary mounting apparatus 300 with prongs 320 that have a sleeve 338 that is advanced by downward force or a threaded mechanism, and then locked in a compressed position with a half-turn mechanism. The prongs 320 may have outcroppings so that when the outer sleeve or nut 338 is advanced over the prongs 320, they are forced inward instead of just to the diameter of the nut 338. As shown in FIG. 4A, an inner surface 321 of the prongs 320 may protrude or overhang the remainder of the prongs 320 to enhance the clamping or compressing feature. Another feature of this design may include a knurled or otherwise textured inner surface 322 of the prongs 320, best seen in FIG. 4B, which also resists extraction of the device.

Figure 5C:
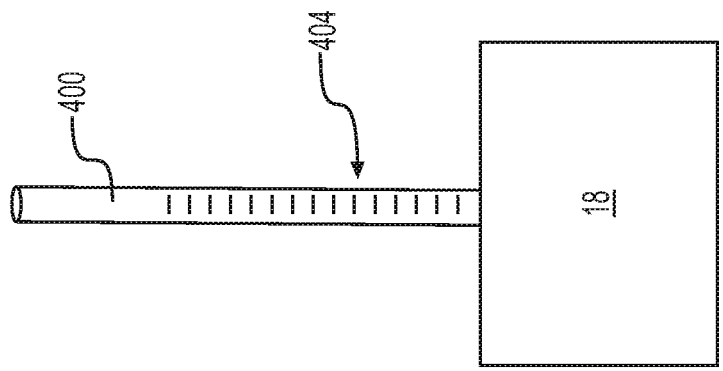
FIGS. 5A-5C show a device suitable to help guide a temporary mounting apparatus into position in the bony structure, for example, when positioning the temporary mounting apparatus through deep layers of soft tissue.
Figure 5B:
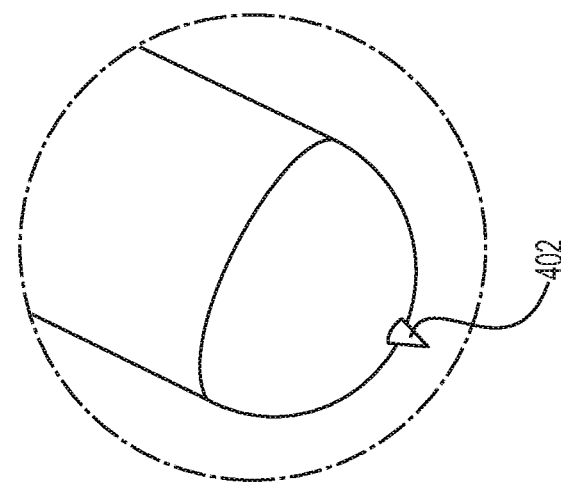
Figure 5A:
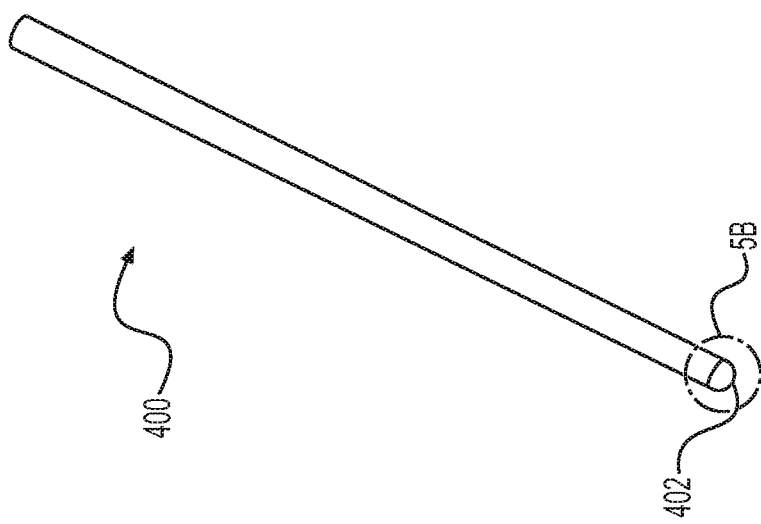

Another embodiment, depicted in FIGS. 5A-5C, may be useful when placing the temporary mount apparatus 10, 100, 200, 300 into bone 18 through deep layers of soft tissue such as skin, fat, and muscle. For example, when attaching a 4-prong spike (e.g., apparatus 10, 100, 200, or 300) to the iliac crest in a large patient, the spike may need to penetrate through several inches of soft tissue before reaching bone 18. If the devices 10, 100, 200, 300, described herein, were to be used after slicing a small starter hole through the soft tissue, the prongs 12, 112, 212, 312 could snag on the soft tissue as it was advanced downwardly well before the prongs 12, 112, 212, 312 start to engage bone 18. By way of example, a central shaft 400 can first be inserted, followed by one of the devices 10 (configured with aperture 16 extending through the device), 200 (configured with aperture 216 extending through the device), 100 or 300 (modified such that it is hollow or cannulated centrally). After the device 10, 100, 200, 300 is in place and inserted desirably in the bone 18, then the central shaft 400 can be removed.

The first step may be to position the central shaft 400 next to bone 18. An example of such a central shaft 400 is shown in FIG. 5A. For example, it may be roughly 10-25 mm in diameter and 150-250 mm long. The shaft 400 may have a tooth 402 on a distal tip that serves to help pin it to bone 18 without wandering along the bone surface. The tooth 402 may be positioned centrally in line with a central longitudinal axis of the device 400. Alternatively, more than one tooth 402 may be positioned at an alternate position on the distal tip of the central shaft 400. The surgeon could use manual force or malleting to push the shaft 400 downward through soft tissue until they felt it hit bone 18. The path of entry could be established freehand or guided using navigation or a robot.

One benefit of using the central shaft 400 as the initial penetrator of soft tissue is that it can be used to gauge the size of the device 10, 100, 200, 300 that will ultimately be needed. As shown in FIG. 5C, graduated markings 404 may be provided along the length of the shaft 400 such that the markings 404 can be read at the level of the skin or at the level of the desired attachment. Using these graduated markings 40, the surgeon may determine where the tracking array would ultimately be located. Based on this location, the appropriate sized cannulated device 10, 100, 200, 300 could be selected from a set of options. Thus, a plurality of different mounts 10, 100, 200, 300, for example, of different sizes and different configurations may be provided as kit. Such a kit may also include the central shaft 400 as well as other tools suitable for the surgery, for example, including the attachable components, such as tracking arrays and the like.

As depicted in FIG. 6, the steps of implanting device 10 with the central shaft 400 are shown. Although described with reference to mount 10, it is understood that these steps would apply equally to the other cannulated devices 100, 200, and 300 described herein.

As shown in step (a1), once the distal tip of the shaft 400 is in place against bone 18, the proximal end of the central shaft 400 could be held in one of the surgeon's hands, left in place by friction, or held by an assistant or robot. As shown in step (b1) the cannulated temporary mount 10 is advanced over the central shaft 400. As shown in step (c1), the pronged mount 10 comes down into contact with the bone 18. The central shaft 400 and mount 10 can be designed so that the prongs 20 hug the shaft 400, preventing soft tissue from getting snagged between the prongs 20 and the shaft 400.

If the cannulated device 10 is longer than the central shaft 400, then striking the cannulated device 10 with a mallet would drive it into the bone 18 as described above for the device 10. After the device 10 is in place the central shaft 400 could be left in place or retrieved with a tool such as a threaded rod that is threaded into a socket in the central shaft 400 (not shown). It may not be desirable to leave the central shaft 400 in place. When left in place while striking the cannulated device 10, there would be a risk that once the device 10 advanced past the point of the end of the central shaft 400, further malleting could undesirably force the central shaft 400 into the bone 18. Instead, the dimensions of the device 10 may be such that the central shaft 400 is longer than the device 10.

Alternatively, a sleeve member 406 could be used in order to drive the device 10 down over the central shaft 400. The sleeve member 406 may optionally include a head portion. In the design of the driving sleeve 406, the enlarged head may be larger in diameter than the rest of the shaft to serve as a larger surface area for striking the piece. As can be seen in alternative step (a2), the shaft 400 is positioned with the device 10 in contact with the bone 18. In step (b2), the sleeve member 406 is positioned over the central shaft 400 and into contact with the device 10. In step (c2), the surgeon would mallet the sleeve member 406, causing advancement of the spike 10. Then, the sleeve member 400 would be removed as shown in step (d2). Subsequently, in step (e2), the central shaft 400 would be removed, and the device 10 would be left embedded in the bone 18. These components may be added and removed one-by-one or together. The desired attachment such as a navigation array could then be placed on and attached to the device 10 using suitable techniques known in the art.

After navigation is complete and/or after the surgical operation is complete, but before the patient is closed, the device 10, 100, 200, 300 can be removed, for example, by pulling it out, prying it out, or using a slap-hammer attached to the aperture 16, 216 or a threaded socket on the device 10, 100, 200, 300. The device 10, 100, 200, 300 can be sterilized for re-use. Alternately, the device 10, 100, 200, and 300 may be used as a disposable part.

The designs for the mounts 10, 100, 200, 300 described herein have advantages over the existing methods of using a single nail or spearhead shaped device. In particular, there are multiple points of fixation (e.g., four points of fixation) through cortical and into cancellous bone instead of just a single point found in traditional nails and the like. This plurality of fixation points provides for strong attachment to the bone 18 and improved accuracy of an attached apparatus, such as a tracker for surgical navigation. The prongs 20, 120, 220, 320 are also designed to be delicate enough that they deform while they are driven into bone 18 to improve the rigidity of fixation. The temporary mounting devices 10, 100, 200, 300 may also include one or more stops such that there is less of a chance of accidentally advancing the device 10, 100, 200, 300 too far into the bone than often occurs with a single nail or spearhead. Thus, the design of the temporary mounts 10, 100, 200, 300 can help to protect the bone 18 and surrounding areas and can be easier to remove from the bone 18 when the surgical navigation and/or surgical procedure are completed.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all ranges broadly recited in this document include within their scope all narrower ranges which fall within the broader ranges. It is also intended that the components of the various devices disclosed above may be combined or modified in any suitable configuration.

What is claimed is:

1. A method of temporarily affixing a temporary mount to a bony structure, comprising:
   inserting a central shaft through soft tissue and into contact with bone;
   inserting a cannulated temporary mount over the central shaft and moving the temporary mount downwardly and into contact with the bony structure, the cannulated temporary mount having a first end and a second end terminating as a plurality of elongated prongs, wherein each of the plurality of elongated prongs are separated a distance from one another, and wherein the plurality of elongated prongs are configured to move inwardly toward one another when driven downward into the bony structure;
   positioning a driving sleeve over the central shaft and into contact with the first end of the temporary mount;
   applying a force to the driving sleeve to cause the temporary mount to advance into the bony structure; and
   removing the driving sleeve and the central shaft to leave the temporary mount embedded in the bony structure.

2. The method of claim 1, wherein the temporary mount includes an outer sleeve, and the method further comprising rotating the outer sleeve in order to compress the plurality of elongated prongs inwardly toward one another to further secure the mount to the bony structure.

3. The method of claim 1, further comprising:
   attaching a portion of a trackable reference array for surgical navigation to the temporary mount.

4. The method of claim 3, further comprising:
   removing the temporary mount from the bony structure after the surgical navigation is complete.

5. The method of claim 1, wherein the temporary mount has multiple points of fixation with the bony structure.

6. The method of claim 1, wherein the plurality of elongated prongs includes four or more prongs extending from a base member.

7. The method of claim 6, wherein the plurality of elongated prongs extend a length greater than a length of the base member.

8. The method of claim 6, wherein the plurality of elongated prongs include a first prong, a second prong, a third prong, and a fourth prong, wherein a first arched portion between the first prong and the second prong has a first distance from a top face of the base member, and a second arched portion from the second prong to the third prong has a second distance from the top face, the second distance being greater than the first distance.

9. The method of claim 6, further comprising:
impacting the base member is impacted with an insertion device to drive the elongated prongs downward, wherein when the base member is impacted, the temporary mount provides an audible sound, and as each of the elongated prongs is driven downward, a frequency of the audible sound changes indicating when the temporary mount is fully seated in the bone structure.

10. The method of claim 1, wherein each of the plurality of elongated prongs includes a protrusion extending therefrom configured to act as a stop to prevent over-insertion of the temporary mount in the bony structure.

11. The method of claim 10, wherein each protrusion is a hill-shaped prominence.

12. The method of claim 1, wherein the plurality of elongated prongs includes a first prong and a second prong, and a transition from the first prong to the second prong is arched to provide an ultimate stop to prevent over-insertion of the temporary mount in the bony structure.

13. The method of claim 1, wherein each of the plurality of elongated prongs have a textured inner surface configured to resist extraction from the bony structure.

14. The method of claim 1, wherein each of the plurality of elongated prongs have a distal-most tip configured to penetrate the bony structure.

15. The method of claim 1, wherein the temporary mount is configured to hold and engage a portion of a trackable reference array for surgical navigation.

16. The method of claim 1, wherein the bony structure is a vertebra of a spine.

* * * * *